US008808875B2

(12) United States Patent
Kamatani et al.

(10) Patent No.: US 8,808,875 B2
(45) Date of Patent: Aug. 19, 2014

(54) COMPOUND AND ORGANIC EL DEVICE

(75) Inventors: Jun Kamatani, Tokyo (JP); Shinjiro Okada, Kamakura (JP); Takao Takiguchi, Chofu (JP); Akihito Saitoh, Yokohama (JP); Keiji Okinaka, Kawasaki (JP); Satoshi Igawa, Fujisawa (JP); Naoki Yamada, Inagi (JP); Masashi Hashimoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 987 days.

(21) Appl. No.: 12/298,300

(22) PCT Filed: Apr. 19, 2007

(86) PCT No.: PCT/JP2007/059000
§ 371 (c)(1),
(2), (4) Date: Oct. 23, 2008

(87) PCT Pub. No.: WO2007/125976
PCT Pub. Date: Nov. 8, 2007

(65) Prior Publication Data
US 2009/0096368 A1    Apr. 16, 2009

(30) Foreign Application Priority Data
Apr. 25, 2006    (JP) ................ 2006-120806

(51) Int. Cl.
*H01J 1/63*        (2006.01)
*C07C 25/13*       (2006.01)
*C07C 43/205*      (2006.01)
*H05B 33/14*       (2006.01)
*H01L 51/00*       (2006.01)
*C09K 11/06*       (2006.01)
*C07C 13/66*       (2006.01)
*H01L 51/50*       (2006.01)

(52) U.S. Cl.
CPC .... *H01L 51/0054* (2013.01); *C09K 2211/1007* (2013.01); *H05B 33/14* (2013.01); *C09K 2211/1011* (2013.01); *C09K 11/06* (2013.01); *H01L 51/5012* (2013.01); *C07C 2103/40* (2013.01); *C07C 13/66* (2013.01); *Y10S 428/917* (2013.01)
USPC ........ 428/690; 428/917; 428/411.1; 428/336; 570/129

(58) Field of Classification Search
USPC ....................................................... 428/690
See application file for complete search history.

(56) References Cited

U.S. PATENT DOCUMENTS

| 2002/0022151 | A1 | 2/2002 | Ishikawa et al. | 428/690 |
| 2004/0232409 | A1* | 11/2004 | Igarashi et al. | 257/40 |
| 2005/0236974 | A1 | 10/2005 | Suzuki et al. | 313/504 |
| 2007/0063189 | A1* | 3/2007 | Schwalm et al. | 257/40 |
| 2007/0104977 | A1* | 5/2007 | Arakane et al. | 428/690 |
| 2007/0252141 | A1 | 11/2007 | Negishi et al. | 257/40 |
| 2008/0124577 | A1 | 5/2008 | Saitoh et al. | 428/704 |
| 2008/0272692 | A1 | 11/2008 | Hashimoto et al. | 313/504 |

FOREIGN PATENT DOCUMENTS

| JP | 10-189247 | 7/1998 | |
| JP | 10-189248 | 7/1998 | |
| JP | 10189248 A * | 7/1998 | ............ H05B 33/14 |
| JP | 2000-007587 | 1/2000 | |
| JP | 2000-007594 | 1/2000 | |
| JP | 2002-043058 | 2/2002 | |
| JP | 2004-107326 | 4/2004 | |
| JP | 2005-068087 | 3/2005 | |
| JP | 2005-235787 | 9/2005 | |
| WO | WO 2004-020371 A1 | 3/2004 | |
| WO | WO 2005/026088 * | 3/2005 | ............ C08C 13/00 |

OTHER PUBLICATIONS

Machine English translation of JP 10-189248 A. Apr. 13, 2012.*
International Preliminary Report on Patentability dated Oct. 28, 2008 for PCT/JP2007/059000.

Chinese Office Action issued in corresponding application No. 200780014786.0 dated Sep. 30, 2011—9 pages.

* cited by examiner

*Primary Examiner* — J. L. Yang

(74) *Attorney, Agent, or Firm* — Fitzpatrick, Cella, Harper & Scinto

(57) ABSTRACT

The present invention provides a high-performance organic EL device and a novel compound used for the device. The novel compound of the present invention is a fluoranthene compound having the following general formula (2):

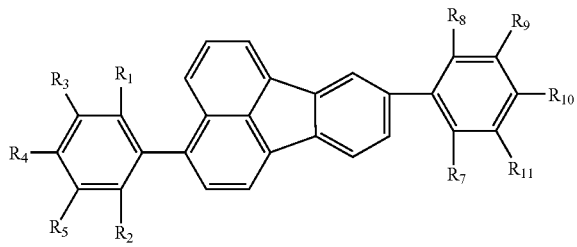

The organic EL device of the present invention is an organic EL device comprising: an anode; a cathode; and an organic compound layer interposed between the anode and the cathode, wherein the organic compound layer has the fluoranthene compound.

10 Claims, 3 Drawing Sheets

COMPOUND AND ORGANIC EL DEVICE

TECHNICAL FIELD

The present invention relates to a novel organic compound and a light-emitting device having the compound.

BACKGROUND ART

An organic light-emitting device has a constitution in which a thin film containing a fluorescent organic compound or a phosphorescent organic compound is interposed between an anode and a cathode. Electrons and holes are injected from the respective electrodes so that excitons of the fluorescent compound or of the phosphorescent compound are generated. The organic light-emitting device utilizes light to be radiated upon return of the excitons to a ground state.

A benzofluoranthene compound has been researched (Japanese Patent Application Laid-Open Nos. H10-189247, 2005-235787, 2000-7587, 2000-7594, and 2005-68087).

DISCLOSURE OF THE INVENTION

However, at present, an optical output with additionally high luminance or additionally high conversion efficiency has been needed. In addition, the organic light-emitting device still involves a large number of problems in terms of durability such as a change with elapse of time due to long-term use and deterioration due to an atmospheric gas containing oxygen, moisture or the like. Further, when the application of the device to a full-color display or the like is taken into consideration, the emission of blue, green, or red light with a good color purity is needed. However, a problem concerning the emission has not been sufficiently solved yet.

An object of the present invention is to provide a novel compound and an organic electroluminescence (EL) device having the compound and having an optical output with high efficiency and high luminance. Another object of the present invention is to provide a highly durable organic EL device. Another object of the present invention is to provide an organic EL device that can be easily produced at a relatively low cost.

According to the present invention, there is provided a compound represented by the following general formula (1):

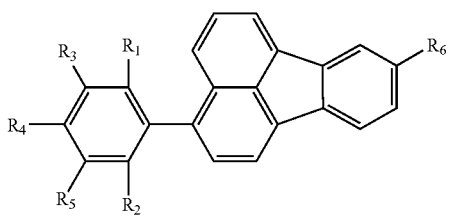

(1)

Wherein $R_1$ and $R_2$ are each independently selected from a halogen atom, a linear or branched alkyl group having 1 to 5 carbon atoms, a diallylamino group which may have a substituent, a silyl group which may have a substituent, an aryl group which may have a substituent, and a heterocyclic group which may have a substituent;

$R_3$ to $R_6$ are each independently selected from a hydrogen atom, a halogen atom, a linear or branched alkyl group having 1 to 5 carbon atoms, a diallylamino group which may have a substituent, a silyl group which may have a substituent, an aryl group which may have a substituent, and a heterocyclic group which may have a substituent; and the substituents are each independently selected from a halogen atom, a linear or branched alkyl group having 1 to 20 carbon atoms (in the alkyl group, one methylene group, or two or more methylene groups not adjacent to each other may be replaced by —O—, —S—, —CO—, —CO—O—, —O—CO—, —CH=CH—, or —C≡C—, and one methylene group, or two or more methylene groups may be replaced by an arylene group or a divalent heterocyclic group; and a hydrogen atom of the alkyl group may be substituted with a fluorine atom), a diphenylamino group, a triphenylsilyl group, an aryl group, and a heterocyclic group.

The compound of the present invention can be suitably utilized in a light-emitting device. In addition, the light-emitting device of the present invention using such compound in its light-emitting layer is an excellent device capable of not only emitting light with high efficiency but also maintaining high luminance for a long time period. In addition, the device shows a larger current value than that of a conventional device at the same voltage value, so the driving of the device at a low voltage can be expected.

DESCRIPTION OF THE EMBODIMENTS

Figure 1A:
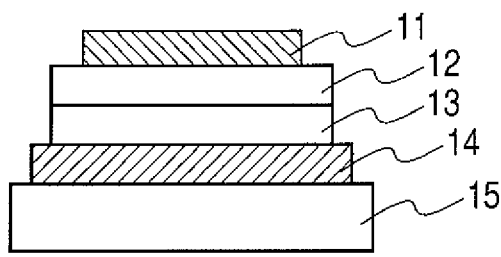
FIGS. 1A, 1B and 1C are schematic views each showing an example of a light-emitting device of the present invention.

The present invention relates to a compound represented by the following general formula (1):

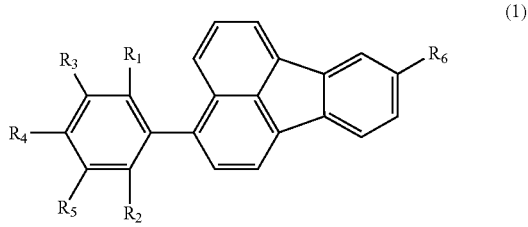

(1)

wherein $R_1$ and $R_2$ are each independently selected from a halogen atom, a linear or branched alkyl group having 1 to 5 carbon atoms, an amino group which may have a substituent, a silyl group which may have a substituent, an aryl group which may have a substituent, and a heterocyclic group which may have a substituent;

$R_3$ to $R_6$ are each independently selected from a hydrogen atom, a halogen atom, a linear or branched alkyl group having 1 to 5 carbon atoms, an amino group which may have a substituent, a silyl group which may have a substituent, an aryl group which may have a substituent, and a heterocyclic group which may have a substituent; and the substituents shown here are each independently selected from a halogen atom, a linear or branched alkyl group having 1 to 20 carbon atoms (in the alkyl group, one methylene group, or two or more methylene groups not adjacent to each other may be replaced by —O—, —S—, —CO—, —CO—O—, —O—CO—, —CH=CH—, or —C≡C—, and one methylene group, or two or more methylene groups may be replaced by an arylene group or a divalent heterocyclic group; and a hydrogen atom of the alkyl group may be substituted with a fluorine atom), a diphenylamino group, a triphenylsilyl group, an aryl group, and a heterocyclic group.

Alternatively, the compound according to the present invention is a compound, among the compounds represented by the above general formula (1), which is represented by the following general formula (2):

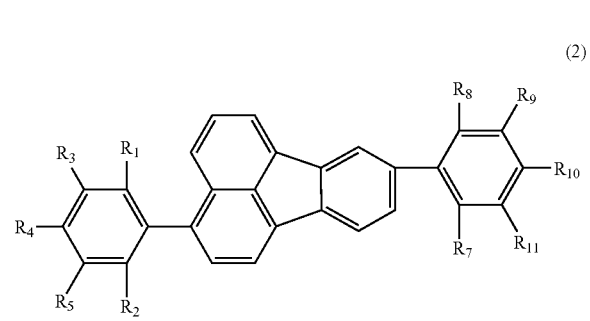

(2)

wherein $R_1$, $R_2$, $R_7$ and $R_8$ are each independently selected from a halogen atom, a linear or branched alkyl group having 1 to 5 carbon atoms, an amino group which may have a substituent, a silyl group which may have a substituent, an aryl group which may have a substituent, and a heterocyclic group which may have a substituent;

$R_3$ to $R_6$ and $R_9$ to $R_{11}$ are each independently selected from a hydrogen atom, a halogen atom, a linear or branched alkyl group having 1 to 5 carbon atoms, an amino group which may have a substituent, a silyl group which may have a substituent, an aryl group which may have a substituent, and a heterocyclic group which may have a substituent; and the substituents shown here are each independently selected from a halogen atom, a linear or branched alkyl group having 1 to 20 carbon atoms (in the alkyl group, one methylene group, or two or more methylene groups not adjacent to each other may be replaced by —O—, —S—, —CO—, —CO—O—, —O—CO—, —CH=CH—, or —C≡C—, and one methylene group, or two or more methylene groups may be replaced by an arylene group or a divalent heterocyclic group; and a hydrogen atom of the alkyl group may be substituted with a fluorine atom), a diphenylamino group, a triphenylsilyl group, an aryl group, and a heterocyclic group.

Alternatively, the compound according to the present invention is a compound, among the compounds represented by the above general formula (1), which is represented by the following general formula (3):

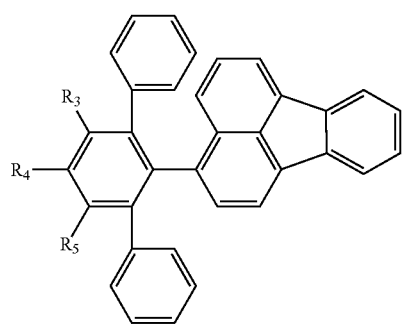

(3)

Alternatively, the compound according to the present invention is a compound, among the compounds represented by the above general formula (2), which is represented by the following general formula (4):

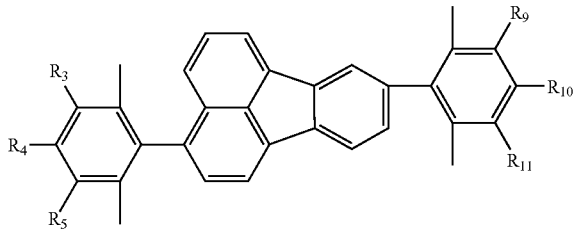

(4)

In addition, the organic EL device according to the present invention is an organic electroluminescent device (organic EL device) including at least one layer containing an organic compound between a pair of electrodes.

In addition, the organic EL device according to the present invention is an organic EL device in which the layer containing the organic compound is a light-emitting layer.

In addition, the organic EL device according to the present invention is an organic electroluminescent device in which the layer containing the organic compound is a light-emitting layer, the light-emitting layer is composed of at least a compound as a host and a compound as a guest, and at least one of the host and the guest is the above organic compound.

In addition, the organic EL device according to the present invention is an organic EL device in which light emission from the guest is fluorescent emission.

Further description is given below.

When a light emitting layer is formed of a carrier transportable host material and a guest, a main process for light emission includes the following several steps of:

1. transporting an electron or a hole in the light emitting layer;
2. generating an exciton of the host material;
3. transferring excitation energy between host material molecules; and
4. moving of the excitation energy from the host material to the guest.

Desired energy movement in each step and light emission occur in competition with various deactivation steps.

Needless to say, the emission quantum yield of a light emission central material itself must be large in order that the emission efficiency of an EL device may be improved. However, the efficiency with which energy movement between host molecules or between host and guest molecules can be performed is also of a great concern. In addition, the deterioration of light emission due to supply of current is assumed to be related to a change in environment surrounding a light emitting material due to at least the light emission central material itself or a molecule around the light emission central material, though no causes for the deterioration have been revealed at present.

In view of the foregoing, the inventors of the present invention have made various studies. As a result, the inventors have found that an organic EL device using a compound represented by the general formula (1) as an electron transport layer or a light-emitting layer, preferably a host or guest for the light-emitting layer, emits light with high efficiency, keeps high luminance for a long time period, and shows small deterioration of light emission due to supply of current.

One possible cause for the deterioration of light emission due to supply of current is the generation of an excimer between guest molecules due to the migration of a guest in a light-emitting layer. When the molecules of a light-emitting material has a shape in which the overlapping extent of the conjugate planes of the molecules is large as in the case of fluoranthene, the probability that an excimer is generated between the molecules is high, so the insufficiency of light-emitting sites due to the fact that the guest is not used at a high concentration, or quenching between light-emitting molecules due to the migration is apt to occur.

Accordingly, such design that fluoranthane is used as a luminous core, and the core portion is covered without any expansion of a conjugate plane can provide a light-emitting device having high efficiency and showing a small color change even at a high concentration. Specifically, the realization of such light-emitting device was attained by introducing a phenyl group as a substituent into fluoranthane and by substituting two hydrogen atoms at ortho-positions of the phenyl group with skeletons each having an atomic radius larger than that of a hydrogen atom to obtain the compound of the present invention.

In addition, when a phenyl group having substituents other than a hydrogen atom at its ortho-positions is introduced into fluoranthene, fluoranthene and the phenyl group change their structures in the direction of losing planarity between fluoranthene and the phenyl group as compared to that in the case where the phenyl group has no substituents at its ortho-positions. The structural change progresses in the direction of breaking conjugation between fluoranthene and the phenyl group, so the case where the phenyl group has substituents at its ortho-positions can exert an effect of shortening the luminous wavelength as compared to that in the case where the phenyl group has no substituents at its ortho-positions.

As described above, the use of the compound of the present invention in a light-emitting layer is effective. The use of the compound in an electron transport layer, a hole transport layer, an electron blocking layer, a hole blocking layer, an electron injection layer, or a hole injection layer is also effective.

An organic layer containing the compound of the present invention can be produced by, for example, a vacuum vapor deposition method, a cast method, an application method, a spin coating method, or an ink-jet method.

In addition, among the substituents, the diallylamino group includes a diphenylamino group, a naphthylphenylamino group, and a dinaphthylamino group.

Figure 1B:
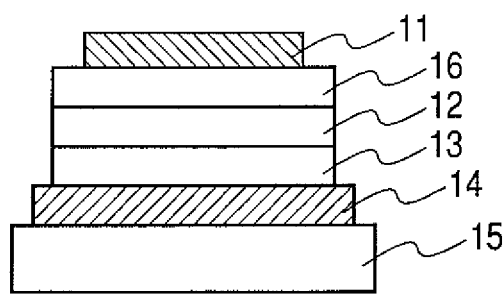
Figure 1C:
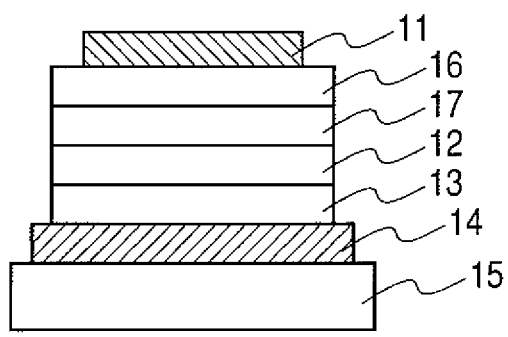

FIGS. 1A, 1B and 1C each show the basic device constitution of the present invention.

As shown in FIGS. 1A, 1B and 1C, an organic EL device generally has a constitution that a transparent electrode 14 having a thickness of 50 nm or more to 200 nm or less, a plurality of organic layers, and a metal electrode 11 are formed on a transparent substrate 15 so as to interpose the organic layers between the electrodes.

FIG. 1A shows an example in which the organic layers are composed of a light-emitting layer 12 and a hole transport layer 13. For example, ITO having a large work function is used in the transparent electrode 14 so that the injection of a hole from the transparent electrode 14 into the hole transport layer 13 is facilitated. A metal material having a small work function such as aluminum, magnesium, or an alloy thereof is used in the metal electrode 11 so that the injection of an electron into the organic layers is facilitated.

The compound of the present invention is used in the light-emitting layer 12. A material having electron-donating property such as a triphenyldiamine derivative typified by α-NPD can be appropriately used in the hole transport layer 13.

A device having the above-mentioned constitution exhibits electrical rectifying property. When an electric field is applied so that the metal electrode 11 serves as a cathode and the transparent electrode 14 serves as an anode, an electron is injected from the metal electrode 11 into the light-emitting layer 12, and a hole is injected from the transparent electrode 14 into the light-emitting layer 12.

The injected hole and electron recombine in the light-emitting layer 12 to generate an exciton, whereby light is emitted. In this case, the hole transport layer 13 serves as an electron blocking layer. As a result, the efficiency of recombining a hole and an electron at an interface between the light-emitting layer 12 and the hole transport layer 13 improves, and hence the emission efficiency of the device improves.

Further, in FIG. 1B, an electron transport layer 16 is provided between the metal electrode 11 and the light-emitting layer 12 as shown in FIG. 1A. A light-emitting function, and electron- and hole-transporting functions are separated from one another so that the constitution of a device is more effective in blocking a carrier. As a result, the emission efficiency of the device improves. For example, an oxadiazole derivative can be used in the electron transport layer 16.

In addition, four-layered constitution as shown in FIG. 1C is also desirable, in which four layers, that is, the hole transport layer 13, the light-emitting layer 12, an exciton diffusion prevention layer 17, and the electron transport layer 16, and the metal electrode 11 are provided in the stated order from the side of the transparent electrode 14 as an anode.

Specific structural formulae of organic compounds to be used in the present invention are shown below.

These formulae are merely representative examples, and the present invention is not limited to them.

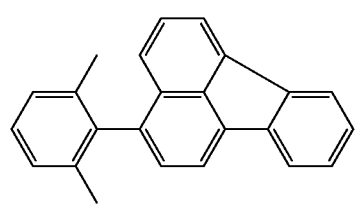

F-1

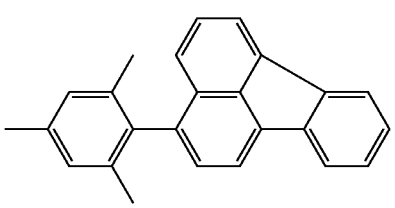

F-2

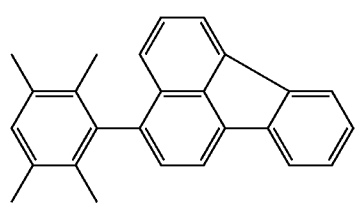

F-3

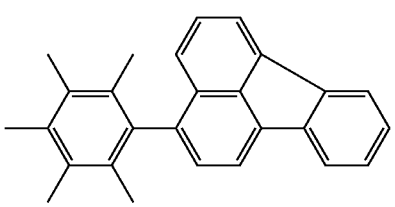

F-4

F-5
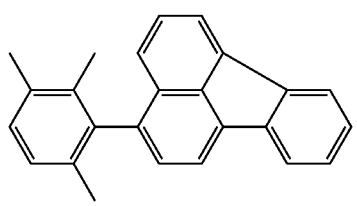
F-6
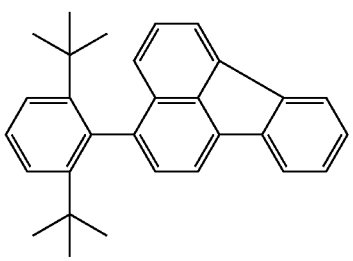
F-7
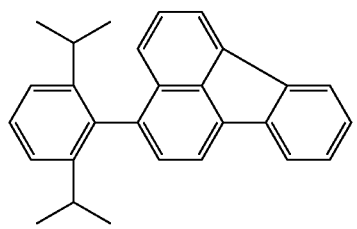
F-8
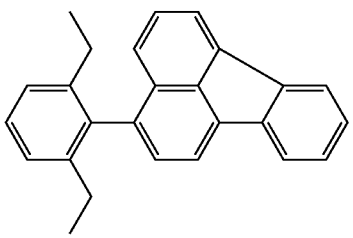
F-9
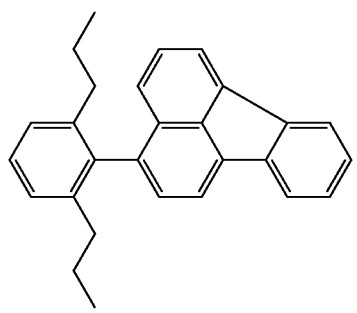
F-10
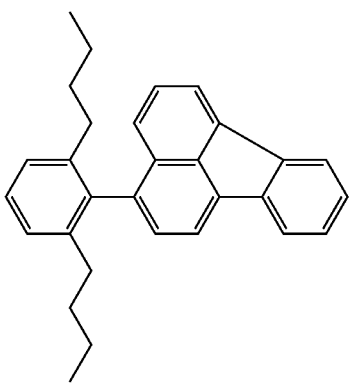
F-11
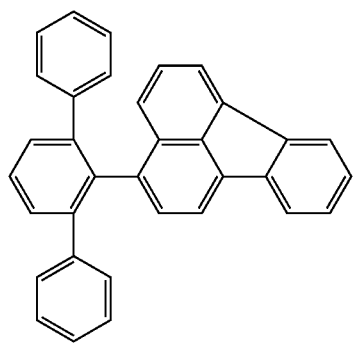
F-12
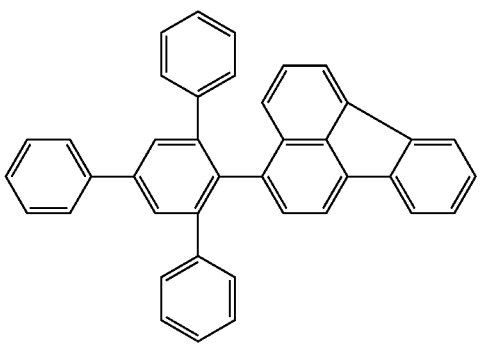
F-13
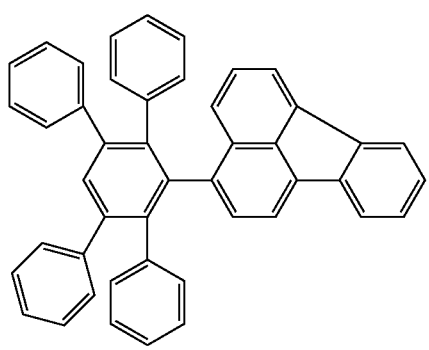
F-14
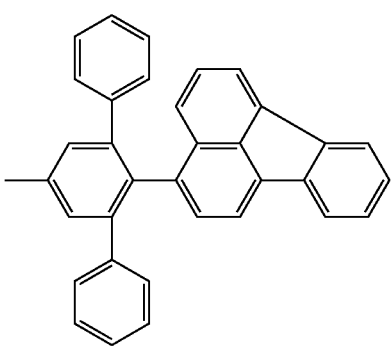

-continued
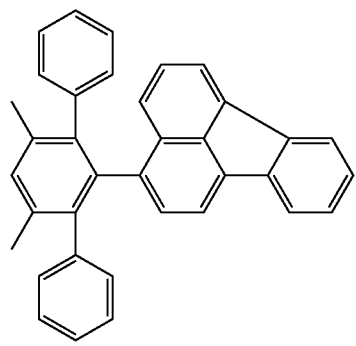
F-15
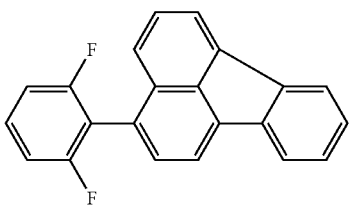
F-16
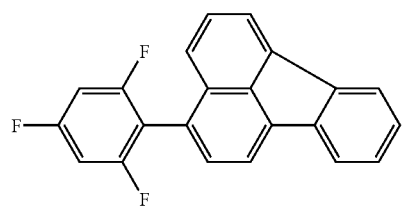
F-17
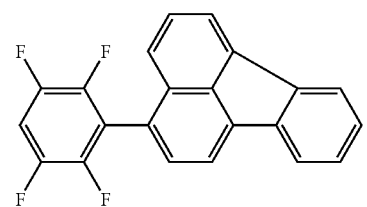
F-18
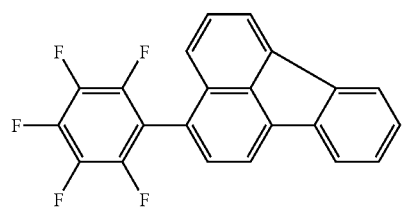
F-19
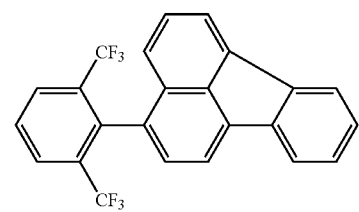
F-20
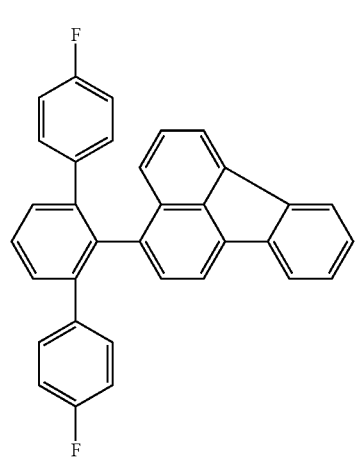
F-21
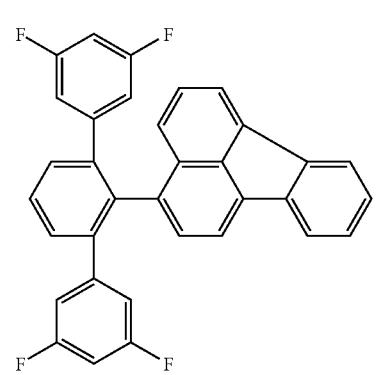
F-22
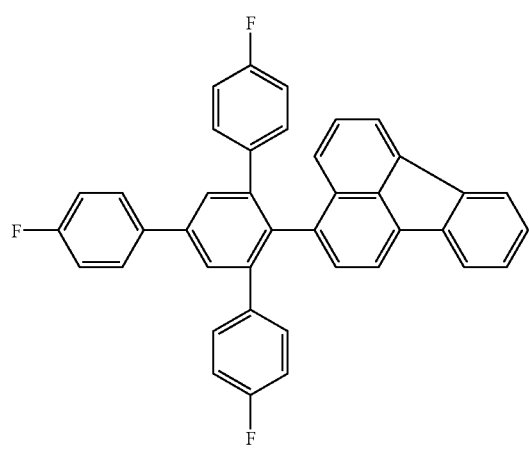
F-23
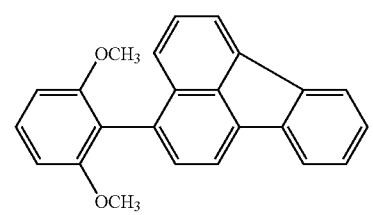
F-24

-continued
F-25
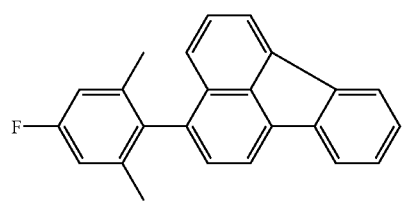
F-26
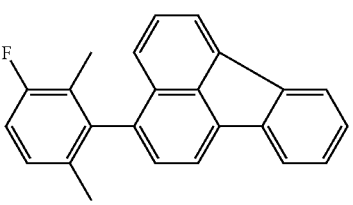
F-27
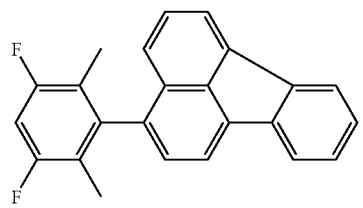
F-28
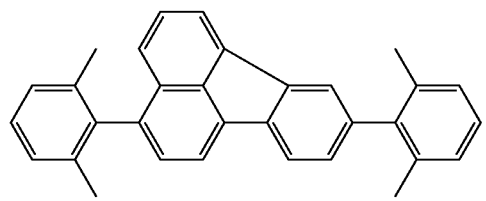
F-29
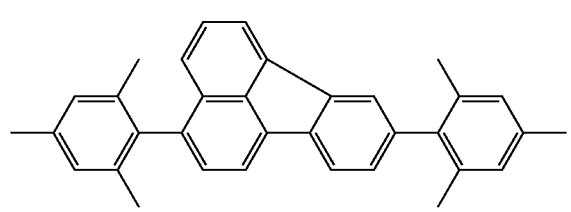
F-30
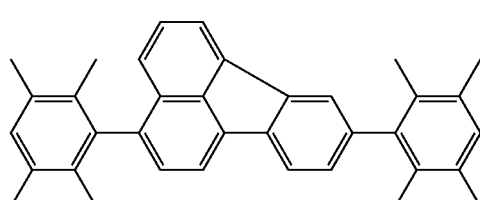
F-31
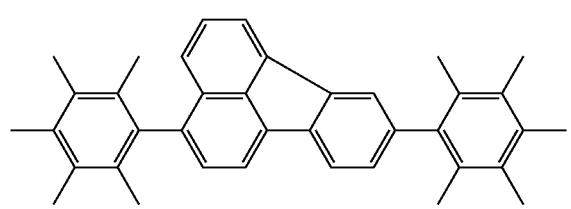
F-32
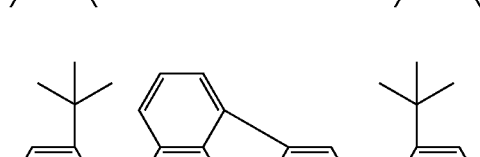
F-33
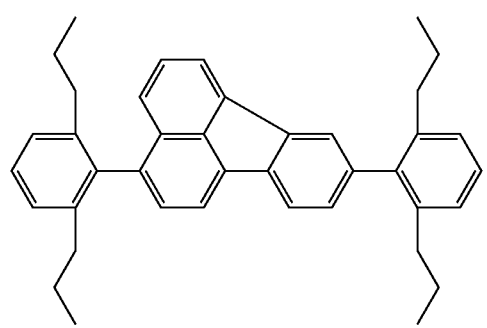
F-34
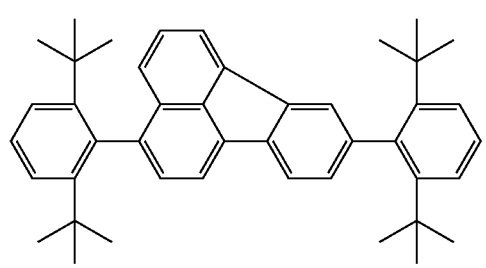
F-35
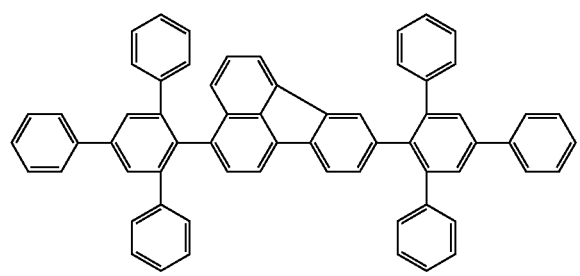
F-36
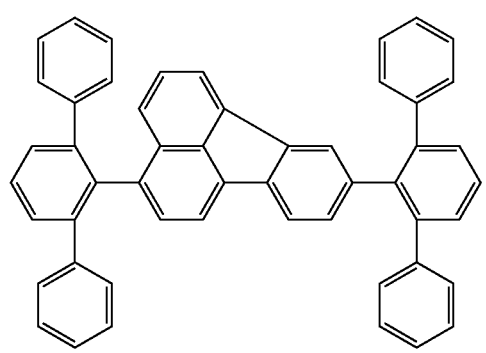

-continued
F-37
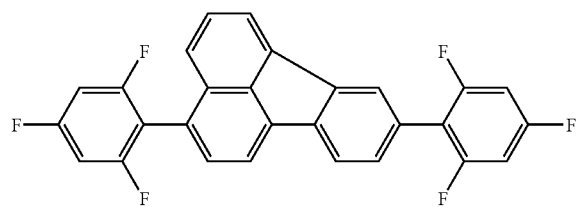
F-38
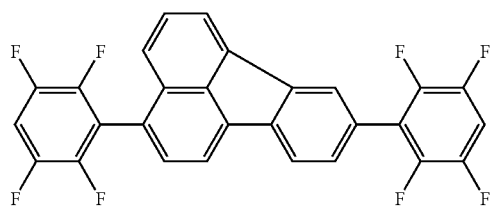
F-39
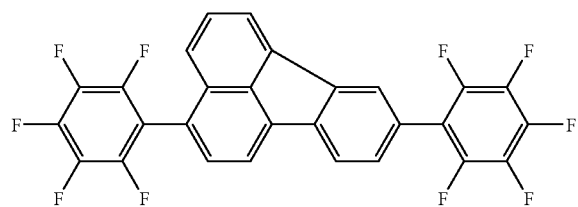
F-40
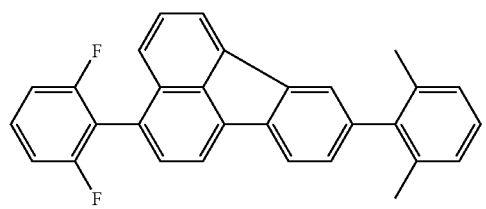
F-41
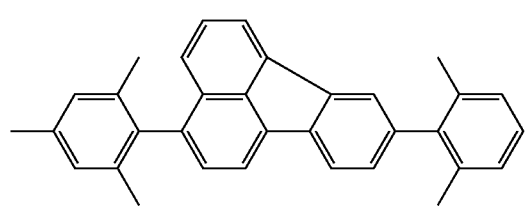
F-42
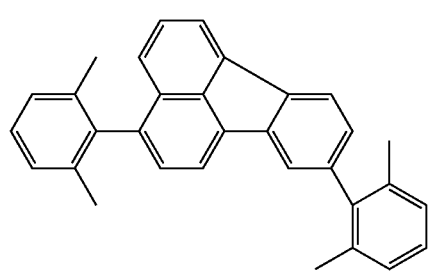
F-43
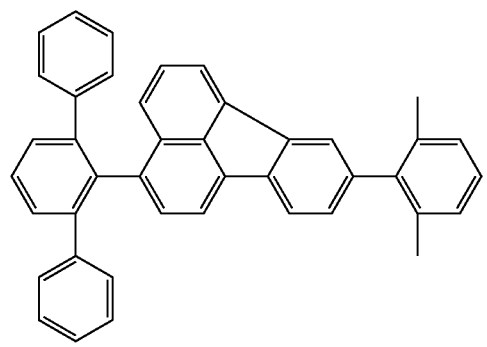
F-44
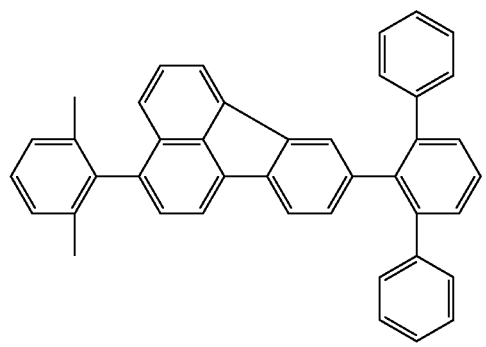
F-45
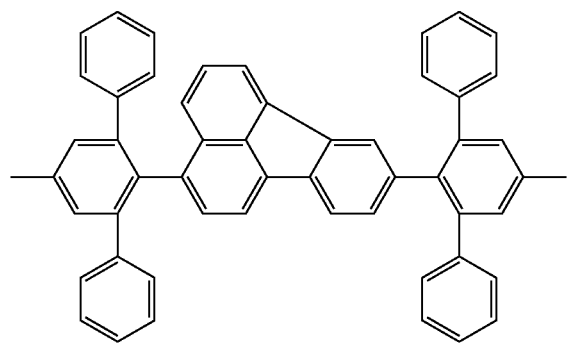
F-46
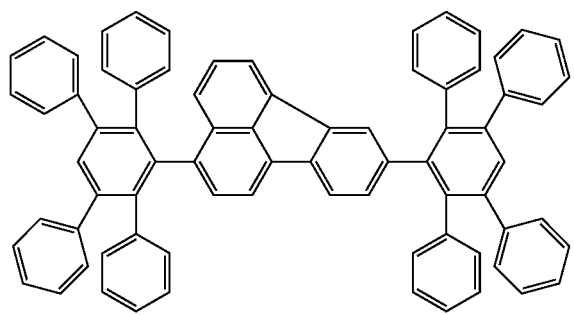

-continued
F-47
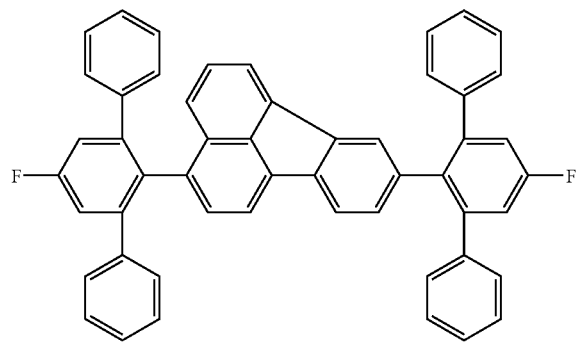
F-48
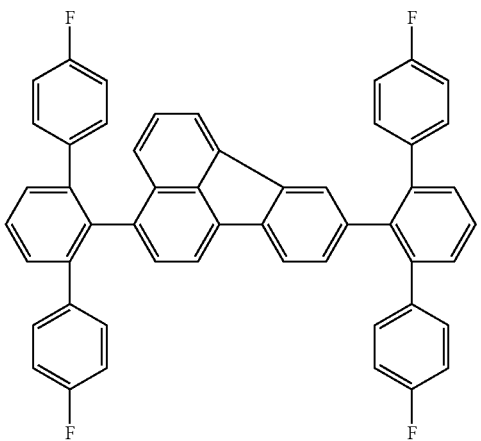
F-49
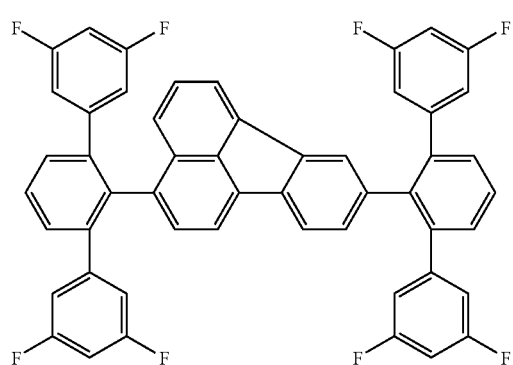
F-50
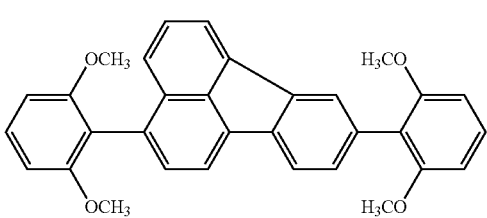
F-51
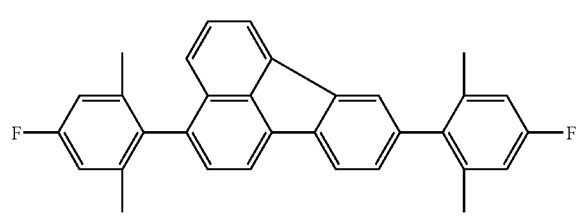
F-52
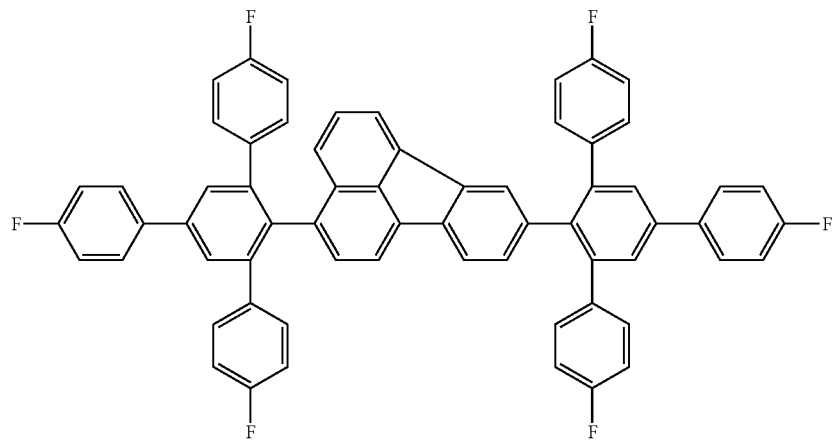

-continued

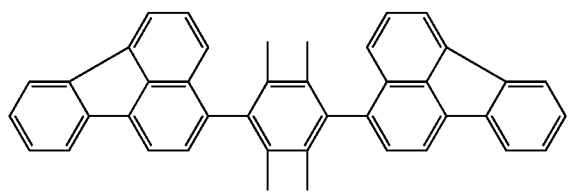

F-53

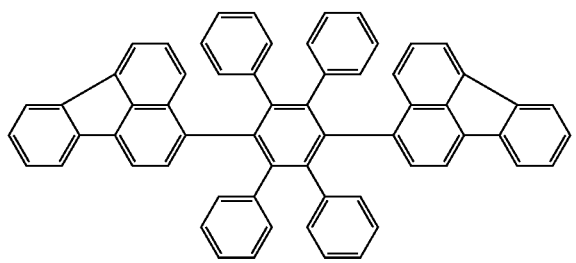

F-54

Hereinafter, the present invention will be specifically described with referring to the following examples, but the present invention is not limited to them.

Example 1

Synthesis of Exemplified Compound No. F-28

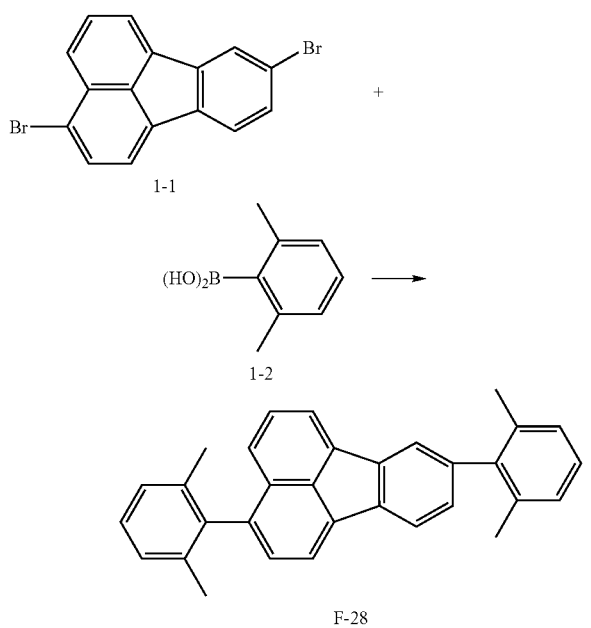

360 mg (1 mmole) of Compound 1-1, 450 mg (3 mmole) of Compound 1-2 (manufactured by SIGMA-ALDRICH), 0.1 g of Pd(PPh3)4, 10 ml of toluene, 5 ml of ethanol, and 10 ml of a 2M aqueous solution of sodium carbonate were charged into a 100-ml egg plant flask, and the mixture was stirred in a stream of nitrogen at 80° C. for 8 hours. After the completion of the reaction, the crystal was separated by filtration, and was washed with water and ethanol. After having been subjected to hot filtration with toluene, the resultant crystal was recrystallized with toluene/heptane and dried in a vacuum at 120° C., whereby 356 mg of Exemplified Compound No. F-28 were obtained (yield: 87%).

Figure 2:
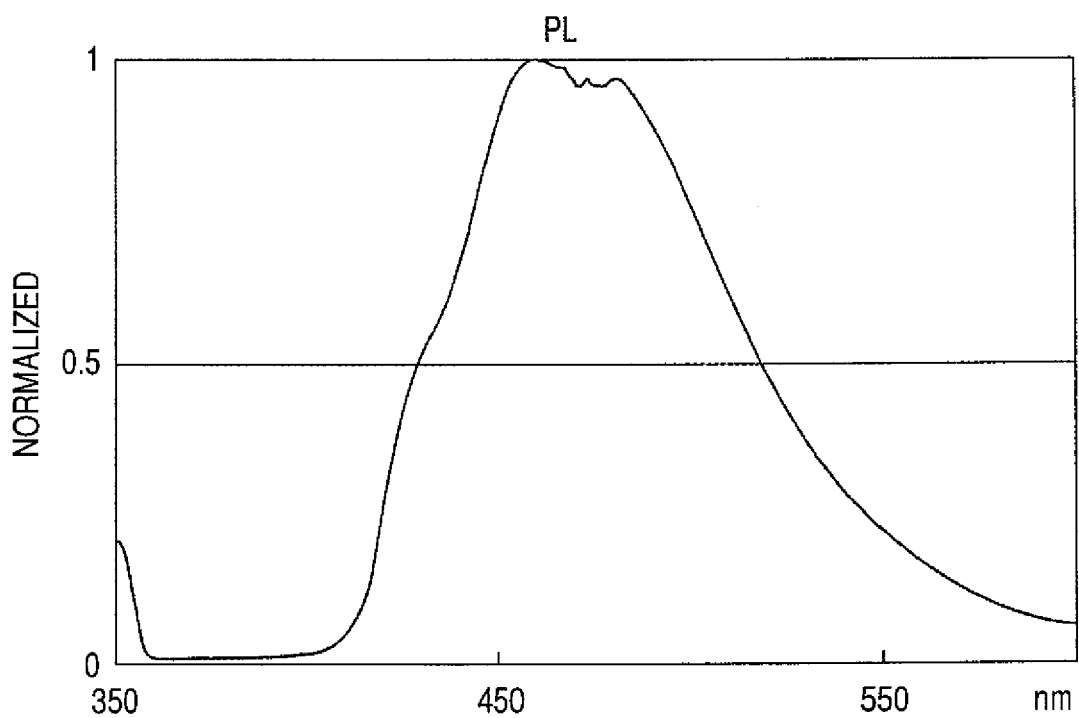
FIG. 2 is a graph showing the light-emitting characteristics of Exemplified Compound No. F-28 in toluene.

FIG. 2 shows the graph of the light-emitting characteristics of the compound in toluene.

Example 2

In this example, a device having such device constitution including three organic layers as shown in FIG. 1B was used.

ITO was patterned onto a glass substrate to form a pattern having a thickness of 100 nm. The following organic layers and electrode layers were continuously formed on the resultant ITO substrate by vacuum vapor deposition using resistance heating in a vacuum chamber at a pressure of $10^{-5}$ Pa so that an opposing electrode area was 3 $mm^2$.

Device A:
　Hole transport layer (20 nm): Compound A
　Light-emitting layer (25 nm): Exemplified Compound No. F-28 (weight ratio 5%):Compound B
　Electron transport layer (40 nm): Bphen
　Metal electrode layer 1 (1 nm): KF
　Metal electrode layer 2 (100 nm): Al

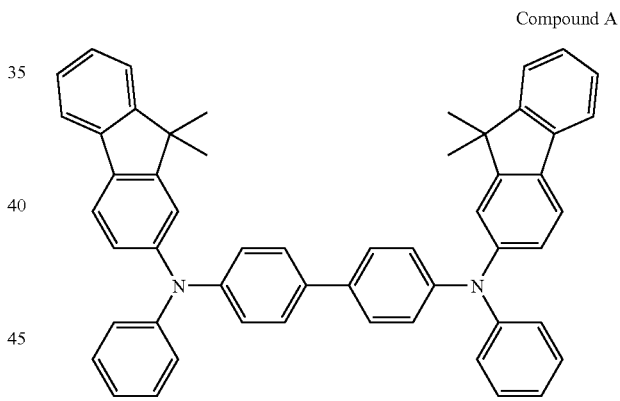

Compound A

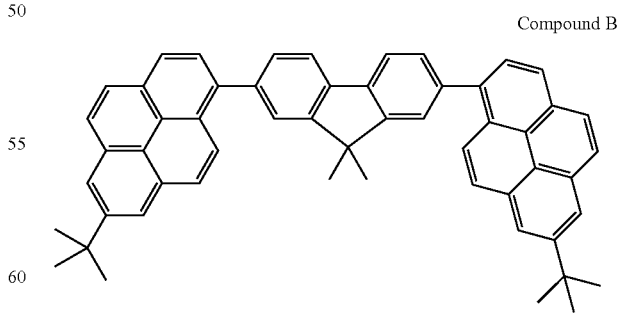

Compound B

The current-voltage characteristics of the EL device were measured with a microammeter 4140B manufactured by Hewlett-Packard Company, and the emission luminance of the device was measured with a BM7 manufactured by TOP- CON CORPORATION. As a result, the observation of light emission derived from Exemplified Compound No. F-28 was attained.

Example 3

Synthesis of Exemplified Compound No. F-11)

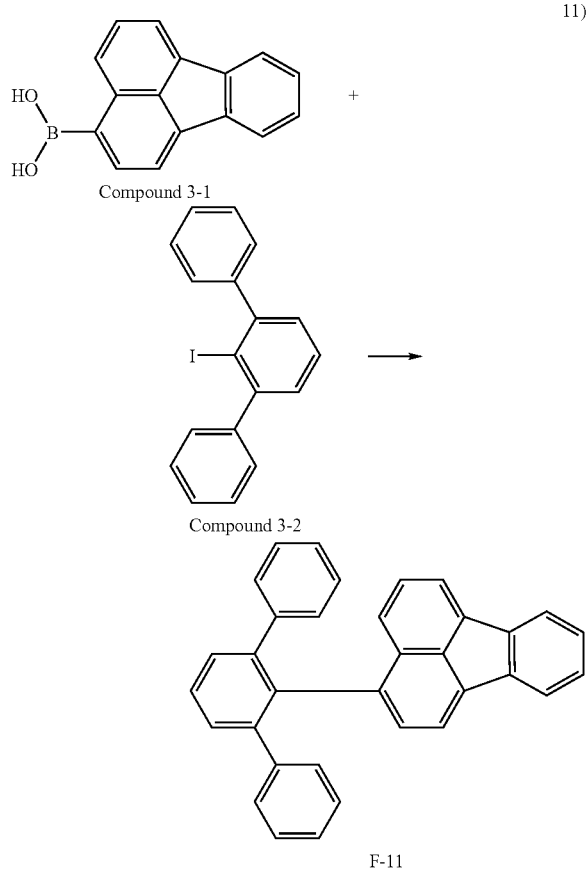

984 mg (4 mmole) of Compound 3-1, 1,420 mg (4 mmole) of Compound 3-2, 0.1 g of Pd(PPh3)4, 20 ml of toluene, 10 ml of ethanol, and 20 ml of a 2-M aqueous solution of sodium carbonate were charged into a 200-ml egg plant flask, and the mixture was stirred in a stream of nitrogen at 80° C. for 8 hours. After the completion of the reaction, the crystal was separated by filtration, and was washed with water and ethanol. After having been subjected to hot filtration with toluene, the resultant crystal was recrystallized with toluene/heptane and dried in a vacuum at 120° C., whereby 900 mg of Exemplified Compound No. F-11 were obtained (yield: 72%).

Figure 3:
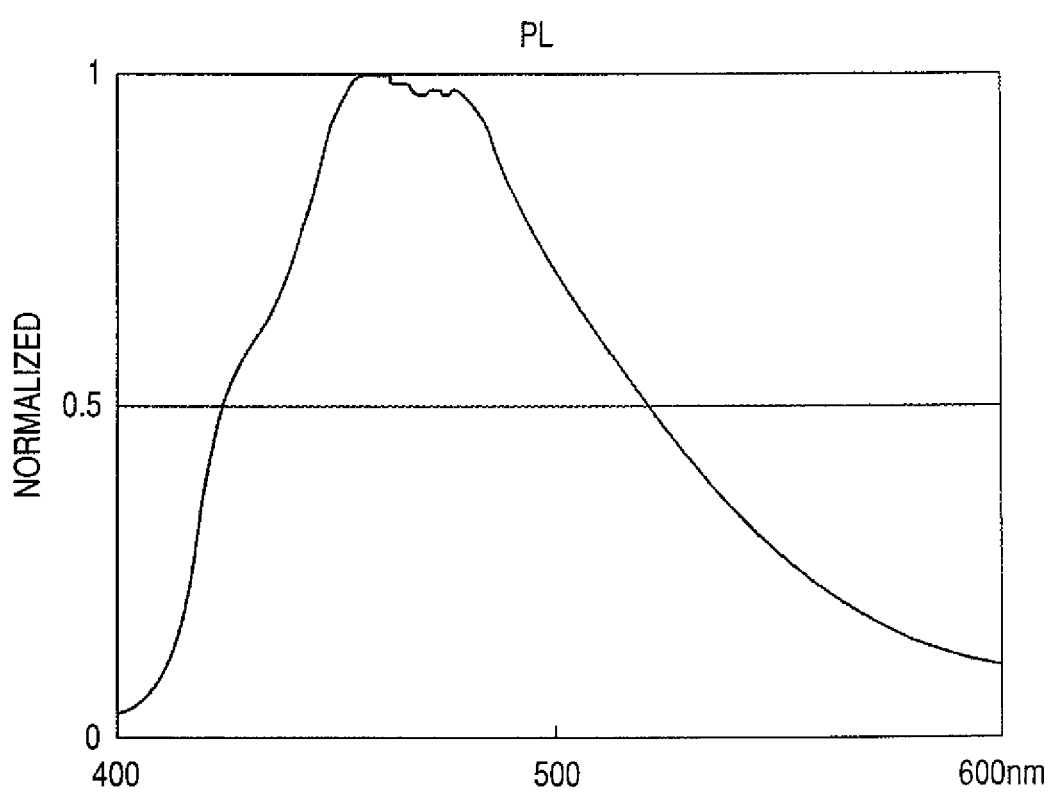
FIG. 3 is a graph showing the light-emitting characteristics of Exemplified Compound No. F-11 in toluene.

FIG. 3 shows the graph of the light-emitting characteristic of the compound in toluene.

Matrix-assisted laser desorption/ionization time-of-flight mass spectrometry (MALDI-TOF MS) confirmed that the compound had an M+ of 430.1.

A device was produced in the same manner as in Example 2 except that Exemplified Compound No. F-11 was used instead of Exemplified Compound No. F-28 of Example 2. As a result, the observation of light emission was attained.

This application claims the benefit of Japanese Patent Application No. 2006-120806, filed Apr. 25, 2006, which is hereby incorporated by reference herein in its entirety.

The invention claimed is:

1. A compound represented by the following general formula (2):

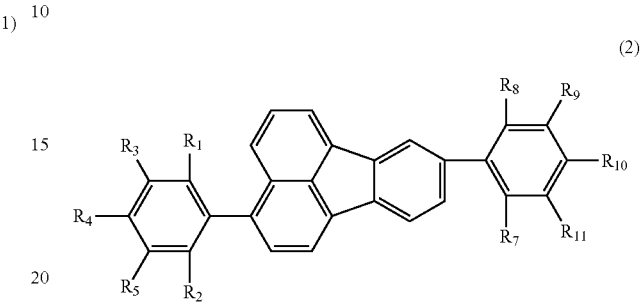

(2)

wherein $R_1$ and $R_2$ are the same and selected from a halogen atom and a linear or branched alkyl group having 3 to 5 carbon atoms;
wherein $R_3$ to $R_5$ are each a hydrogen atom;
wherein $R_7$ and $R_8$ are the same and are a linear or branched alkyl group having 3 to 5 carbon atoms; and
wherein $R_9$ to $R_{11}$ are each a hydrogen atom.

2. An organic EL device comprising:
an anode;
a cathode; and
an organic compound layer interposed between the anode and the cathode,
wherein the organic compound layer has the compound of general formula (2) according to claim 1.

3. The organic EL device according to claim 2, wherein the organic compound layer is a light-emitting layer.

4. The organic EL device according to claim 3, wherein the light-emitting layer has a host and a guest, and the host is the compound of general formula (2).

5. The organic EL device according to claim 3, wherein the light-emitting layer has a host and a guest, and the guest is the compound of general formula (2).

6. The organic EL device according to claim 3, wherein the light-emitting layer has a host and a guest, and the host and the guest each are independently selected from the compound of general formula (2).

7. A full-color display comprising the organic EL device according to claim 3, wherein the display emits blue, green, or red light.

8. A full-color display comprising the organic EL device according to claim 4, wherein the display emits blue, green, or red light.

9. A full-color display comprising the organic EL device according to claim 5, wherein the display emits blue, green, or red light.

10. A full-color display comprising the organic EL device according to claim 6, wherein the display emits blue, green, or red light.

* * * * *